United States Patent
Zhu

(10) Patent No.: US 12,397,162 B2
(45) Date of Patent: Aug. 26, 2025

(54) METHOD AND APPARATUS FOR GENERATING MODULATED NEUROSTIMULATION PULSE SEQUENCE

(71) Applicant: Boston Scientific Neuromodulation Corporation, Valencia, CA (US)

(72) Inventor: Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 823 days.

(21) Appl. No.: 17/530,236

(22) Filed: Nov. 18, 2021

(65) Prior Publication Data
US 2022/0184400 A1 Jun. 16, 2022

Related U.S. Application Data

(60) Provisional application No. 63/125,515, filed on Dec. 15, 2020.

(51) Int. Cl.
*A61N 1/372* (2006.01)
*A61N 1/36* (2006.01)

(52) U.S. Cl.
CPC ..... *A61N 1/36178* (2013.01); *A61N 1/36189* (2013.01); *A61N 1/37247* (2013.01)

(58) Field of Classification Search
CPC ............ A61N 1/36178; A61N 1/37247; A61N 1/36189
See application file for complete search history.

(56) References Cited

U.S. PATENT DOCUMENTS

| 7,664,849 B1 | 2/2010 | Chandler et al. |
| 7,979,119 B2 | 7/2011 | Kothandaraman et al. |
| (Continued) | | |

FOREIGN PATENT DOCUMENTS

| AU | 2015343483 B2 | 6/2018 |
| AU | 2020289746 B2 | 1/2023 |
| (Continued) | | |

OTHER PUBLICATIONS

"U.S. Appl. No. 14/926,725, Corrected Notice of Allowance mailed Jul. 17, 2017", 2 pgs.
(Continued)

*Primary Examiner* — Joseph M Dietrich
(74) *Attorney, Agent, or Firm* — Schwegman Lundberg & Woessner, P.A.

(57) ABSTRACT

An example of a system for delivering neurostimulation may include a programming control circuit and a user interface. The programming control circuit may be configured to generate stimulation parameters controlling delivery of the neurostimulation according to a pulse sequence. The pulse sequence may include a series of neurostimulation pulses and be defined by sequence parameters and one or more modulation functions each modulating an adjustable parameter selected from the sequence parameters. The user interface may be configured to set the pulse sequence to a tonic pulse sequence by determining an initial value for each adjustable parameter and set the pulse sequence to a modulated pulse sequence by selecting one or more adjustable parameters, determining a modulation function for each selected adjustable parameter, and applying the determined modulation function to that selected adjustable parameter to modulate the tonic pulse sequence.

20 Claims, 11 Drawing Sheets

(56) References Cited

U.S. PATENT DOCUMENTS

| | | | |
|---|---|---|---|
| 7,983,762 | B2 | 7/2011 | Gliner et al. |
| 8,560,080 | B2 | 10/2013 | Goetz |
| 9,474,905 | B2 | 10/2016 | Doan et al. |
| 9,737,717 | B2 | 8/2017 | Moffitt et al. |
| 9,802,052 | B2 | 10/2017 | Marnfeldt |
| 10,118,040 | B2* | 11/2018 | Zhu .................. A61N 1/36071 |
| 10,195,439 | B2 | 2/2019 | Steinke et al. |
| 10,213,608 | B2 | 2/2019 | Moffitt |
| 10,335,599 | B2 | 7/2019 | Zottola |
| 10,449,360 | B2 | 10/2019 | Moffitt et al. |
| 10,456,586 | B2 | 10/2019 | Wechter et al. |
| 11,224,750 | B2 | 1/2022 | Zhu |
| 11,684,779 | B2 | 6/2023 | Zhu |
| 12,070,606 | B2 | 8/2024 | Zhu |
| 2011/0208012 | A1 | 8/2011 | Gerber et al. |
| 2011/0270348 | A1 | 11/2011 | Goetz |
| 2012/0184801 | A1 | 7/2012 | Simon et al. |
| 2014/0046398 | A1 | 2/2014 | Sachs et al. |
| 2014/0067016 | A1 | 3/2014 | Kaula et al. |
| 2016/0121126 | A1 | 5/2016 | Marnfeldt |
| 2016/0246935 | A1 | 8/2016 | Cerny et al. |
| 2016/0279429 | A1 | 9/2016 | Hershey et al. |
| 2016/0346546 | A1* | 12/2016 | Zhu .................. A61N 1/36071 |
| 2017/0143964 | A1* | 5/2017 | Zhu .................. A61N 1/36192 |
| 2017/0304636 | A1 | 10/2017 | Steinke et al. |
| 2019/0054306 | A1 | 2/2019 | Steinke et al. |
| 2019/0126029 | A1 | 5/2019 | Cheeran et al. |
| 2019/0160295 | A1 | 5/2019 | Moffitt |
| 2019/0184180 | A1 | 6/2019 | Zhang et al. |
| 2019/0329024 | A1* | 10/2019 | Kothandaraman .......................... A61N 1/36171 |
| 2019/0366107 | A1 | 12/2019 | Moffitt |
| 2020/0147397 | A1 | 5/2020 | Huertas Fernandez et al. |
| 2022/0118260 | A1 | 4/2022 | Zhu |

FOREIGN PATENT DOCUMENTS

| | | |
|---|---|---|
| CN | 102413870 A | 4/2012 |
| CN | 102725023 A | 10/2012 |
| CN | 202933390 U | 5/2013 |
| CN | 203777499 U | 8/2014 |
| CN | 107073269 A | 8/2017 |
| CN | 107073269 B | 5/2020 |
| CN | 107921261 B | 1/2022 |
| EP | 2958618 B1 | 3/2023 |
| JP | 2017533072 A | 11/2017 |
| JP | 6452936 B2 | 12/2018 |
| WO | WO-2009067610 A1 | 5/2009 |
| WO | WO-2014159880 A1 | 10/2014 |
| WO | WO-2016004230 A1 | 1/2016 |
| WO | WO-2016073271 A1 | 5/2016 |
| WO | WO-2016154375 A1 | 9/2016 |
| WO | WO-2022132380 A1 | 6/2022 |

OTHER PUBLICATIONS

"U.S. Appl. No. 14/926,725, Non Final Office Action mailed Mar. 3, 2017", 13 pgs.

"U.S. Appl. No. 14/926,725, Notice of Allowability mailed Jul. 28, 2017", 2 pgs.

"U.S. Appl. No. 14/926,725, Notice of Allowance mailed Jun. 27, 2017", 8 pgs.

"U.S. Appl. No. 14/926,725, Response filed May 25, 2017 to Non Final Office Action mailed Mar. 3, 2017", 12 pgs.

"U.S. Appl. No. 15/079,340, Advisory Action mailed Apr. 8, 2019", 3 pgs.

"U.S. Appl. No. 15/079,340, Advisory Action mailed Jun. 21, 2018", 3 pgs.

"U.S. Appl. No. 15/079,340, Examiner Interview Summary mailed Mar. 5, 2019", 3 pgs.

"U.S. Appl. No. 15/079,340, Examiner Interview Summary mailed Jun. 17, 2019", 3 pgs.

"U.S. Appl. No. 15/079,340, Final Office Action mailed Jan. 10, 2019", 13 pgs.

"U.S. Appl. No. 15/079,340, Final Office Action mailed Apr. 4, 2018", 12 pgs.

"U.S. Appl. No. 15/079,340, Non Final Office Action mailed May 13, 2019", 13 pgs.

"U.S. Appl. No. 15/079,340, Non Final Office Action mailed Jul. 27, 2018", 12 pgs.

"U.S. Appl. No. 15/079,340, Non Final Office Action mailed Oct. 3, 2017", 10 pgs.

"U.S. Appl. No. 15/079,340, Response filed Mar. 4, 2019 to Final Office Action mailed Jan. 10, 2019", 12 pgs.

"U.S. Appl. No. 15/079,340, Response filed Jun. 4, 2018 to Final Office Action mailed Apr. 4, 2018", 10 pgs.

"U.S. Appl. No. 15/079,340, Response filed Oct. 29, 2018 to Non Final Office Action mailed Jul. 27, 2018", 10 pgs.

"U.S. Appl. No. 15/079,340, Response filed Dec. 20, 2017 to Non Final Office Action mailed Oct. 3, 2017", 10 pgs.

"U.S. Appl. No. 15/079,340, Supplemental Amendment and Response Apr. 10, 2019", 14 pgs.

"Australian Application Serial No. 2015343483, First Examiners Report mailed Sep. 19, 2017", 3 pgs.

"Australian Application Serial No. 2015343483, Response filed Feb. 8, 18 to First Examiners Report mailed Sep. 19, 2017", 17 pgs.

"Chinese Application Serial No. 201580060184.3, Response filed Oct. 9, 2019 to Office Action mailed Aug. 2, 2019", w/ English claims, 14 pgs.

"Chinese Application Serial No. 201580060184.3, Response to Examiner Telephone Interview filed Jan. 7, 2020", w/ English claims, 13 pgs.

"European Application Serial No. 15791183.5, Response filed Feb. 6, 2018 to Communication Pursuant to Rules 161 & 162 EPC mailed Jul. 27, 2017", 12 pgs.

"International Application Serial No. PCT/US15/58017, International Search Report mailed Apr. 6, 2016", 5 pgs.

"International Application Serial No. PCT/US15/58017, Written Opinion mailed Apr. 6, 2016", 8 pgs.

"International Application Serial No. PCT/US2015/058017, International Preliminary Report on Patentability mailed May 18, 2017", 10 pgs.

"International Application Serial No. PCT/US2016/023888, International Preliminary Report on Patentability mailed Oct. 5, 2017", 7 pgs.

"International Application Serial No. PCT/US2016/023888, International Search Report mailed Jun. 6, 2016", 5 pgs.

"International Application Serial No. PCT/US2016/023888, Written Opinion mailed Jun. 6, 2016", 5 pgs.

"Japanese Application Serial No. 2017-542797, Office Action mailed May 21, 2018", with English translation, 4 pgs.

"Japanese Application Serial No. 2017-542797, Response filed Aug. 17, 2018 to Office Action mailed May 21, 2018", w/ English claims, 9 pgs.

Carlson, Dave, et al., "A Flexible Algorithm Framework for Closed-Loop Neuromodulation Research Systems", Annual International Conference of the IEEE EMBS, (2013), 6146-6150.

Huiling, Zhao, et al., "A new type of intelligent electric stimulation", Chinese Medical Equipment, vol. 8, Issue 10, (Oct. 31, 2011), 1-4.

Moffitt, Michael A., et al., "Graphical User Interface for Programming Neurostimulation Pulse Patterns", U.S. Appl. No. 14/853,589, filed Sep. 14, 2015.

U.S. Appl. No. 14/926,725 U.S. Pat. No. 9,802,052, filed Oct. 29, 2015, Method and Apparatus for Programming Complex Neurostimulation Patterns.

U.S. Appl. No. 15/079,340, filed Mar. 24, 2016, Method and Apparatus for Controlling Temporal Patterns of Neurostimulation.

"U.S. Appl. No. 17/157,659, Final Office Action mailed May 29, 2024", 20 pgs.

"U.S. Appl. No. 17/157,659, Non Final Office Action mailed Dec. 1, 2023", 14 pgs.

"U.S. Appl. No. 17/157,659, Notice of Allowance mailed Aug. 28, 2024", 9 pgs.

(56) References Cited

OTHER PUBLICATIONS

"U.S. Appl. No. 17/157,659, Preliminary Amendment filed Nov. 1, 2022", 7 pgs.
"U.S. Appl. No. 17/157,659, Response filed Feb. 22, 2024 to Non Final Office Action mailed Dec. 1, 2023", 10 pgs.
"U.S. Appl. No. 17/157,659, Response filed Jul. 29, 2024 to Final Office Action mailed May 29, 2024", 12 pgs.
"U.S. Appl. No. 17/157,659, Response filed Sep. 19, 2023 to Restriction Requirement mailed Jul. 28, 2023", 6 pgs.
"U.S. Appl. No. 17/157,659, Restriction Requirement mailed Jul. 28, 2023", 7 pgs.
"U.S. Appl. No. 17/157,690, Non Final Office Action malled Oct. 7, 2022", 5 pgs.
"U.S. Appl. No. 17/157,690, Notice of Allowance mailed Feb. 21, 2023", 8 pgs.
"U.S. Appl. No. 17/157,690, Response filed Jan. 6, 2022 to Non Final Office Action mailed Oct. 7, 2022", 6 pgs.
"U.S. Appl. No. 17/562,865, Non Final Office Action mailed Jan. 30, 2024", 7 pgs.
"U.S. Appl. No. 17/562,865, Notice of Allowance mailed Apr. 19, 2024", 7 pgs.
"U.S. Appl. No. 17/562,865, Preliminary Amendment filed Jan. 10, 2022", 7 pgs.
"U.S. Appl. No. 17/562,865, Response filed Apr. 2, 2024 to Non Final Office Action mailed Jan. 30, 2024", 7 pgs.
"U.S. Appl. No. 18/770,423, Preliminary Amendment filed Jul. 17, 2024", 6 pgs.
"Australian Application Serial No. 2020289746, First Examination Report malled Mar. 11, 2022", 4 pgs.
"Australian Application Serial No. 2020289746, Response filed Nov. 17, 2022 to First Examination Report mailed Mar. 11, 2022", 6 pgs.
"Australian Application Serial No. 2023201153, First Examination Report mailed May 8, 2024", 3 pgs.
"International Application Serial No. PCT/US2021/059948, International Preliminary Report on Patentability mailed Jun. 29, 2023", 10 pgs.
"International Application Serial No. PCT/US2021/059948, International Search Report mailed Mar. 3, 2022", 5 pgs.
"International Application Serial No. PCT/US2021/059948, Written Opinion mailed Mar. 3, 2022", 8 pgs.

\* cited by examiner

METHOD AND APPARATUS FOR GENERATING MODULATED NEUROSTIMULATION PULSE SEQUENCE

CLAIM OF PRIORITY

This application claims the benefit of priority to U.S. Provisional Application Ser. No. 63/125,515, filed on Dec. 15, 2020, which is hereby incorporated by reference in its entirety.

TECHNICAL FIELD

This document relates generally to medical devices and more particularly to a system for generating modulated pulse sequence for controlling delivery of neurostimulation from a stimulation device.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in a form of electrical signals. The delivery is controlled using stimulation parameters that specify spatial (where to stimulate), temporal (when to stimulate), and informational (patterns of stimulation directing the nervous system to respond as desired) aspects of a pattern of the electrical signals. Efficacy and efficiency of certain neurostimulation therapies can be improved, and their side-effects can be reduced, by determining these stimulation parameters based on a patient's conditions and therapeutic objectives. While modern electronics can accommodate the need for generating sophisticated signal patterns, the capability of a neurostimulation system depends on how stimulation parameters defining such a signal pattern can be generated in an efficient manner for programming a stimulation device such as the implantable neurostimulator.

SUMMARY

An example (e.g., "Example 1") of a system for delivering neurostimulation through electrodes may include a programming control circuit and a user interface. The programming control circuit may be configured to generate a plurality of stimulation parameters controlling delivery of the neurostimulation according to a pulse sequence. The pulse sequence may include a series of neurostimulation pulses and be defined by sequence parameters and one or more modulation functions each modulating a parameter of one or more adjustable parameters selected from the sequence parameters. The user interface is coupled to the programming control circuit and may be configured to set the pulse sequence to a tonic pulse sequence by determining an initial value for each parameter of the one or more adjustable parameters and set the pulse sequence to a modulated pulse sequence by selecting one or more parameters from the one or more adjustable parameters, determining a modulation function for each parameter of the selected one or more adjustable parameters, and applying the determined modulation function to the each parameter to modulate the tonic pulse sequence.

In Example 2, the subject matter of Example 1 may optionally be configured to further include a storage device configured to store the pulse sequence, including the sequence parameters and the one or more modulation functions.

In Example 3, the subject matter of any one or any combination of Examples 1 and 2 may optionally be configured such that the user interface includes a presentation device, a user input device, and an interface control circuit. The presentation device is configured to present a modulation control panel allowing for selection of a parameter from the one or more adjustable parameters and determination of a modulation function of the one or more modulation functions. The determined modulation function is to be applied to the selected parameter. The user input device is configured to receive user input for the determination of the initial value for each parameter of the one or more adjustable parameters and the determination of the modulation function using the presented modulation control panel. The interface control circuit is configured to control the presentation of the modulation control panel and to create the tonic pulse sequence and the modulated pulse sequence using the received user input.

In Example 4, the subject matter of Example 3 may optionally be configured such that the user interface is configured to present the modulation control panel of a plurality of modulation control panels based on a type of the parameter selected from the one or more adjustable parameters.

In Example 5, the subject matter of Example 4 may optionally be configured such that the one or more adjustable parameters include at least one of one or more adjustable waveform parameters or one or more adjustable field parameters, and the one or more modulation functions include at least one of one or more waveform modulation functions or one or more field modulation functions. The one or more adjustable waveform parameters allow for adjustment of a stimulation waveform of the series of neurostimulation pulses. The one or more adjustable field parameters allow for adjustment a stimulation field associated with the stimulation waveform. The stimulation field specifies a distribution of a stimulation energy over the electrodes for each pulse of the series of neurostimulation pulses. The one or more waveform modulation functions each modulate a parameter of the one or more adjustable waveform parameters. The one or more field modulation functions each modulate a parameter of the one or more adjustable field parameters.

In Example 6, the subject matter of Example 5 may optionally be configured such that the user interface is configured to present a waveform modulation control panel in response to a waveform parameter of the one or more adjustable waveform parameters being selected and present a field modulation control panel in response to a field parameter of the one or more adjustable field parameters being selected.

In Example 7, the subject matter of Example 6 may optionally be configured such that the waveform modulation control panel and the field modulation control panel each include an adjustable parameters field configured to display the one or more adjustable parameters and allow for selection of the parameter from the one or more adjustable parameters.

In Example 8, the subject matter of Example 7 may optionally be configured such that the adjustable parameter field is further configured to display indicators for each parameter of the one or more adjustable parameters that has been selected.

In Example 9, the subject matter of any one or any combination of Examples 6 to 8 may optionally be configured such that the one or more adjustable parameters are selected from waveform parameters defining the stimulation waveform and a field parameter defining the stimulation field. The waveform parameters include a pulse amplitude, a pulse width, and a pulse rate.

In Example 10, the subject matter of any one or any combination of Examples 6 to 9 may optionally be configured such that the waveform modulation control panel is configured to allow for the selection the parameter from the one or more adjustable waveform parameters and the one or more adjustable field parameters, allow for determination of a waveform modulation function for modulating the selected parameter in response to the selected parameter being the waveform parameter, and switch to the field modulation control panel in response to the selected parameter being the field parameter.

In Example 11, the subject matter of Example 10 may optionally be configured such that waveform modulation control panel includes a waveform modulation function selection field and a waveform modulation parameters field. The waveform modulation function selection field is configured to present available waveform modulation functions and to allow for selection of a waveform modulation function from the available waveform modulation functions. The waveform modulation parameters field is configured to present waveform modulation parameters associated with the selected waveform modulation function and allow for determination of the waveform modulation parameters.

In Example 12, the subject matter of Example 11 may optionally be configured such that the waveform modulation control panel further includes a waveform modulation function visualization field configured to present the selected waveform modulation function. The presented waveform modulation function is defined by the selected waveform modulation function as presented in the waveform modulation function selection field and the waveform modulation parameters associated with the selected modulation function as presented in the waveform modulation parameters field.

In Example 13, the subject matter of any one or any combination of Examples 11 and 12 may optionally be configured such that the waveform modulation control panel further includes a modulated pulse sequence field configured to present the pulse sequence modulated by the selected waveform modulation function.

In Example 14, the subject matter of any one or any combination of Examples 6 to 13 may optionally be configured such that the field modulation control panel is configured to allow for the selection of the parameter from the one or more adjustable waveform parameters and the one or more adjustable field parameters, allow for determination of a field modulation function for modulating the selected parameter in response to the selected parameter being the field parameter, and switch to the waveform modulation control panel in response to the selected parameter being the waveform parameter.

In Example 15, the subject matter of Example 14 may optionally be configured such that the field modulation control panel includes a field modulation function field and a field modulation parameters field. The field modulation function field is configured to present available field modulation functions and to allow for selection of a field modulation function from the available field modulation functions. The field modulation parameters field is configured to present field modulation parameters associated with the selected field modulation function and allow for determination of the field modulation parameters.

An example (e.g., "Example 16") of a method for delivering neurostimulation through electrodes is also provided. The method may include generating a plurality of stimulation parameters controlling delivery of the neurostimulation according to a pulse sequence. The pulse sequence may include a series of neurostimulation pulses and be defined by sequence parameters and one or more modulation functions each modulating a parameter of one or more adjustable parameters selected from the sequence parameters. The method may further include setting the pulse sequence to a tonic pulse sequence by determining an initial value for each parameter of the one or more adjustable parameters, selecting one or more parameters from the one or more adjustable parameters, determining one or more modulation functions each for a parameter of the selected one or more parameters, and setting the pulse sequence to a modulated pulse sequence by applying the determined one or more modulation functions to the respective selected one or more parameters to modulate the tonic pulse sequence.

In Example 17, the subject matter of Example 16 may optionally further include using a user interface to present a modulation control panel allowing for selection of a parameter from the one or more adjustable parameters and determination of a modulation function of the one or more modulation functions, receive user input for the determination of the initial value for each parameter of the one or more adjustable parameters and the determination of the modulation function using the presented modulation control panel, and control the presentation of the modulation control panel and create the tonic pulse sequence and the modulated pulse sequence using the received user input. The determined modulation function is to be applied to the selected parameter.

In Example 18, the subject matter of Example 17 may optionally further include using the user interface to present the modulation control panel of a plurality of modulation control panels based on a type of the parameter selected from the one or more adjustable parameters.

In Example 19, the one or more adjustable parameters as found in any one or any combination of Examples 16 to 18 may optionally include at least one of one or more adjustable waveform parameters or one or more adjustable field parameters, and the one or more modulation functions as found in any one or any combination of Examples 16 to 18 may optionally include at least one of one or more waveform modulation functions or one or more field modulation functions. The one or more adjustable waveform parameters allow for adjustment of a stimulation waveform of the series of neurostimulation pulses. The one or more adjustable field parameters allow for adjustment a stimulation field associated with the stimulation waveform. The stimulation field specifies a distribution of a stimulation energy over the electrodes for each pulse of the series of neurostimulation pulses. The one or more waveform modulation functions each modulate a parameter of the one or more adjustable waveform parameters. The one or more field modulation functions each modulate a parameter of the one or more adjustable field parameters.

In Example 20, the subject matter of Example 19 may optionally further include using the user interface to present a waveform modulation control panel in response to a waveform parameter of the one or more adjustable waveform parameters being selected and present a field modulation control panel in response to a field parameter of the one or more adjustable field parameters being selected.

In Example 21, the subject matter of Example 20 may optionally further include using the user interface, while the waveform modulation control panel is presented, to receive the selection the parameter from the one or more adjustable waveform parameters and the one or more adjustable field parameters, allow for determination of a waveform modulation function for modulating the selected parameter in response to the selected parameter being the waveform parameter, and switch to the field modulation control panel in response to the selected parameter being the field parameter.

In Example 22, the subject matter of any one or any combination of Examples 20 and 21 may optionally further include using the user interface, while the waveform modulation control panel is presented, to present available waveform modulation functions, receive selection of a waveform modulation function from the available waveform modulation functions, present waveform modulation parameters associated with the selected waveform modulation function, and allow for determination of the waveform modulation parameters.

In Example 23, the subject matter of any one or any combination of Examples 20 to 22 may optionally further include using the user interface, while the field modulation control panel is presented, to receive the selection of the parameter from the one or more adjustable waveform parameters and the one or more adjustable field parameters, allow for determination of a field modulation function for modulating the selected parameter in response to the selected parameter being the field parameter, and switch to the waveform modulation control panel in response to the selected parameter being the waveform parameter.

In Example 24, the subject matter of any one or any combination of Examples 20 to 23 may optionally further include using the user interface, while the field modulation control panel is presented, to present available field modulation functions, receive selection of a field modulation function from the available field modulation functions, present field modulation parameters associated with the selected field modulation function, and allow for determination of the field modulation parameters.

An example (e.g., "Example 25") of a non-transitory computer-readable storage medium including instructions, which when executed by a system, cause the system to perform a method for delivering neurostimulation through electrodes is also provided. The method may include generating a plurality of stimulation parameters controlling delivery of the neurostimulation pulses according to a modulated pulse sequence. The modulated pulse sequence may include a series of neurostimulation pulses and defined by sequence parameters and one or more modulation functions each modulating a parameter of one or more adjustable parameters selected from the sequence parameters. The method may further include determining a tonic pulse sequence by determining an initial value for each parameter of the one or more adjustable parameters, selecting one or more parameters from the one or more adjustable parameters of the tonic pulse sequence, determining one or more modulation function each for a parameter of the selected one or more adjustable parameters, and generating the modulated pulse sequence by applying the determined one or more modulation functions to the respective selected one or more adjustable parameters to modulate the tonic pulse sequence.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
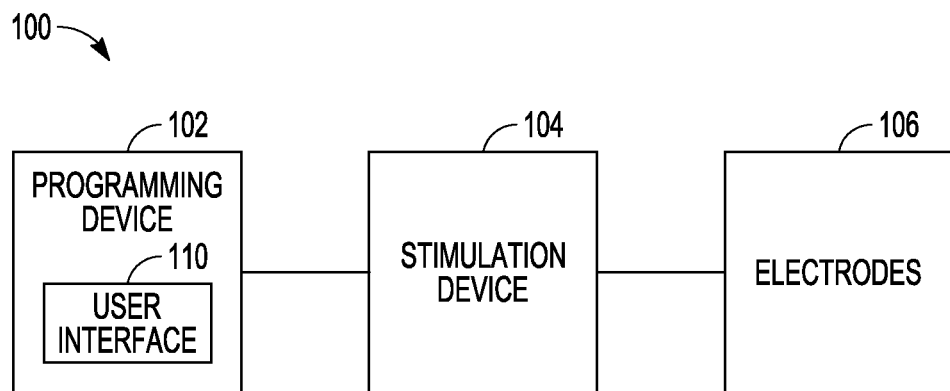
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a method and system for generating stimulation parameters defining a sequence of neurostimulation pulses to control delivery of neurostimulation energy from a stimulation device according to the sequence. Artificial neurostimulation with a pattern of pulses that repeats over time is known to cause accommodation or adaptation, which reduces effectiveness of a neurostimulation therapy over time. A higher level of neurostimulation energy and/or an adjustment of the target stimulation location may be required to maintain or restore efficacy of the therapy. For example, a tonic pulse train may be effective initially but loses effectiveness over time, and there is a practical limit for increasing the intensity of stimulation for safety and energy availability reasons. One approach to reducing or avoiding accommodation is to deliver neurostimulation pulses in a manner that mimics the nature process of nerve recruitment, which involves recruiting different groups of nerves at different time and/or at different firing rates over time. This can be done by defining a sequence of neurostimulation pulses based on nerve recording. The sequence is to elicit action potentials that mimic nature neural signals. Due to the complexity of the natural neural signals, parameters specifying various time-varying aspects of the sequence may need to vary from pulse to pulse. Constructing such a sequence of neurostimulation pulses on a pulse-by-pulse basis may be flexible but inefficient and very time consuming. Thus, there is a need for a more efficient and user-friendly way to construct the sequence.

The present subject matter allows for creation and adjustment of a pulse sequence by generating modulation functions that modulate stimulation parameters that define the pulse sequence. The pulse sequence can include a series of featured neurostimulation pulses (also referred to as a pattern of neurostimulation pulses) each having an individually definable pulse shape and individually definable stimulation parameters (e.g., pulse amplitude, pulse width, and pulse rate, where the pulse rate defines the time interval from the adjacent pulses, either the last pulse or the next pulse). The modulation functions can each be generated for one or more of the individually definable stimulation parameters and applied to the series of neurostimulation pulses to modulate the respective parameter(s) for the pulse sequence. Thus, the pulse sequence can be converted to a different pulse sequence using the modulation functions. This allows multiple patterned pulse sequences to be generated by applying different sets of modulation functions to a pulse sequence. Each modulation function can modulate the value of one or more stimulation parameters such that the value can vary from pulse to pulse. In various embodiments, the modulation functions can be generated for modulating stimulation parameters that can define stimulation waveform and stimulation field on a pulse-by-pulse basis. In some embodiments, some or all of the neurostimulation pulses are grouped into blocks. A modulation function can modulate the value of a stimulation parameter such that the value can vary from block to block for the grouped neurostimulation pulses. The modulation functions can be generated for modulating stimulation parameters that can define stimulation waveform and stimulation field on a pulse-by-pulse and block-by-block basis, depending on the desired resolution of change. In various embodiments, the modulation functions can each be a function of time, a function of pulse number, or a function of order arrangement of groups of pulses. A modulation function of time can specify when the modulation is applied. A modulation function of pulse number can specify to which a stimulation pulse or group of stimulation pulses the modulation is applied. The stimulation pulses or groups of stimulation pulses can be applied in an order of spatial distribution, for example in a linear direction, in a circular direction (clockwise or counter-clockwise), or in specified order of spatial transition. A modulation function of pulse order can specify at which order of stimulation the modulation is applied.

In an example, a tonic pulse sequence (defined by stimulation parameters having constant values) is converted to a patterned pulse sequence (defined by stimulation parameters having time-varying values) by generating modulation functions and applying the modulation functions to the stimulation parameters defining the tonic pulse sequence. A stimulation device is programmed to deliver tonic stimulation to a patient. The stimulation parameters are determined for the tonic stimulation (e.g., optimized by effecting one or more target responses in the patient that can include measurable neural and/or other physiological activities or states). These stimulation parameters can include, for example, stimulation field (location and shape defined by selection of active electrodes or distribution of stimulation energy among electrodes), pulse amplitude, pulse width, pulse rate, and charge balancing (active or passive recharge phase). The tonic pulse sequence includes a series of neurostimulation pulses to be delivered using the determined (e.g., optimized) stimulation parameters, with a sequence duration defined by a time period or a number of the stimulation pulses. This tonic pulse sequence is then converted to a patterned pulse sequence. While the tonic pulse sequence is discussed in this document as an example, the conversion process can start from any template pulse sequence. For example, the modulation function of the modulated parameter in a first pulse sequence can be derived and used to modulate another parameter in a second pulse sequence. In another example, a pulse sequence with a modulation depth of d1 can be rescaled to generate a pulse sequence with a modulation depth of d2. In still another example, a pulse sequence with a basic rate of k0 hertz can be resampled to generate a pulse sequence with a basic rate of k0/n hertz or interpolated to generate a pulse sequence with a basic rate of n*k0 hertz. Similarly, a pulse sequence with a modulation frequency of f0 hertz can be resampled or interpolated to generate a pulse sequence with a modulation frequency of f0/m hertz or m*f0 hertz. In one embodiment, the template pulse sequence is a shared or recommended pulse sequence from another user or patient, and modified to generate a new sequence customed for another patient. In another embodiment, the template is a spiking sequence that specifies the timing of pulse (e.g., a binary sequence representing the presence of pulses or status of modulation). The conversion process can include selecting the stimulation parameters to be modulated and selecting a modulation function for each selected stimulation parameter. For example, the stimulation parameters can be selected from the pulse amplitude, the pulse width, the pulse rate, and the stimulation field, and the modulation function can be selected from predefined, stochastic, and custom functions. A patterned pulse sequence is generated by applying the selected modulation function(s) to the selected stimulation parameter(s). This patterned pulse sequence is used to control delivery of neurostimulation to the patient. The modulation functions can be adjusted based on the patient's response to the delivery of the neurostimulation. The patient response can include, for example, feedback reported from the patient and one or more signals sensed from the patient (e.g., neural signals such as evoked compound action potentials, other physiological signals, and physical activities).

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a series of neurostimulation pulses to be delivered to the patient as well as individual waveforms that are used as building blocks of the series of neurostimulation pulses, such as the waveform of each pulse in the series of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
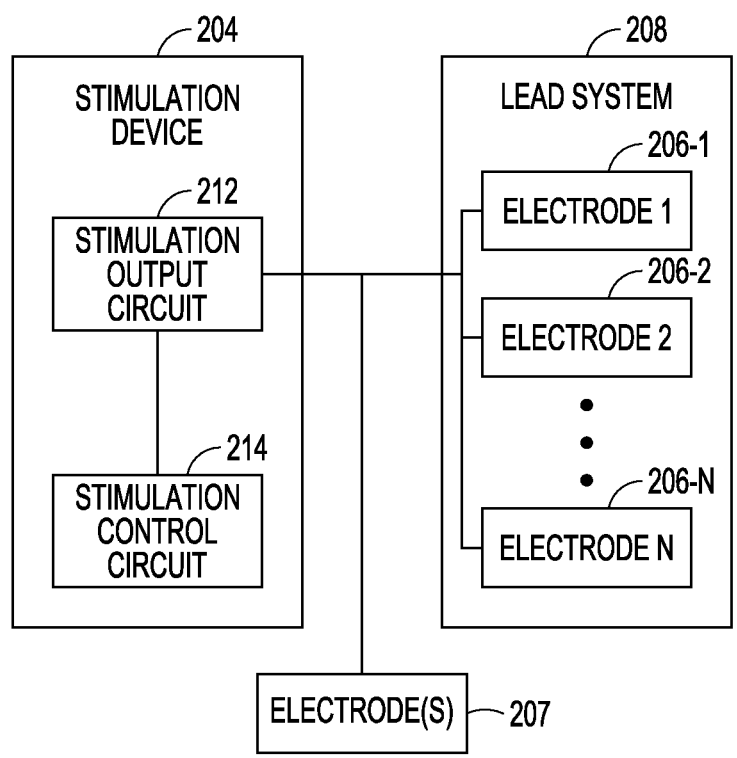
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none of electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
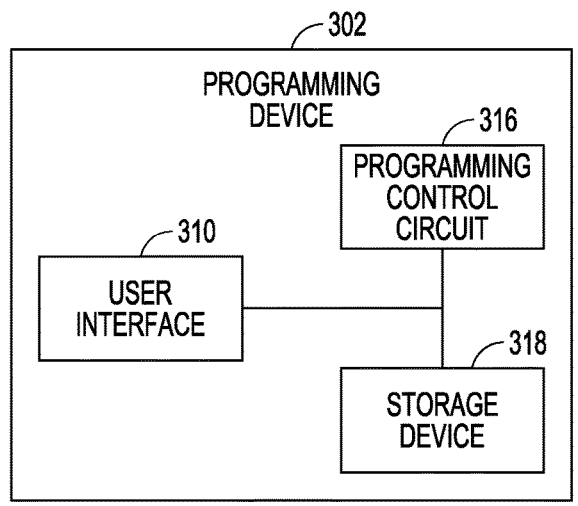
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and can be configured to support one or more functions allowing for programming of stimulation devices, such as stimulation device 104 including its various embodiments as discussed in this document, according to one or more selected neurostimulation programs as discussed in this document. Storage device 318 stores information used by programming control circuit 316 and user interface 310, such as information about a stimulation device that relates the neurostimulation program to the plurality of stimulation parameters.

User interface 310 allows for definition of a pulse sequence including a series of neurostimulation pulses for delivery during a neurostimulation therapy session by creating and/or adjusting one or more stimulation waveforms. The definition can also include definition of one or more stimulation fields each associated with one or more pulses in the series of neurostimulation pulses. As used in this document, a "neurostimulation program" can include the pulse sequence including the one or more stimulation fields, or at least various aspects or parameters of the pulse sequence including the one or more stimulation fields. In various embodiments, user interface 310 includes a GUI that allows the user to define the pulse sequence and perform other functions using graphical methods. In this document, "neurostimulation programming" can include the definition of the one or more stimulation waveforms, including the definition of one or more stimulation fields.

Programming control circuit 316 can be configured to generate a plurality of stimulation parameters controlling delivery of the neurostimulation pulses according to a pulse sequence. The pulse sequence includes a series of neurostimulation pulses and can be defined by sequence parameters and one or more modulation functions each modulating a parameter of one or more adjustable parameters selected from the sequence parameters. User interface 310 can be configured to set the pulse sequence to a tonic pulse sequence (or another template pulse sequence) by determining an initial value for each parameter of the one or more adjustable parameters and to set the pulse sequence to a modulated pulse sequence by selecting one or more parameters from the one or more adjustable parameters, determining a modulation function for each parameter of the selected one or more adjustable parameters, and applying the determined modulation function to the each parameter to modulate the tonic pulse sequence. Storage device can store the pulse sequence, including the sequence parameters and the one or more modulation functions.

In various embodiments, circuits of neurostimulation 100, including its various embodiments discussed in this document, may be implemented using a combination of hardware and software. For example, the circuit of user interface 110, stimulation control circuit 214, and programming control circuit 316, including their various examples discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
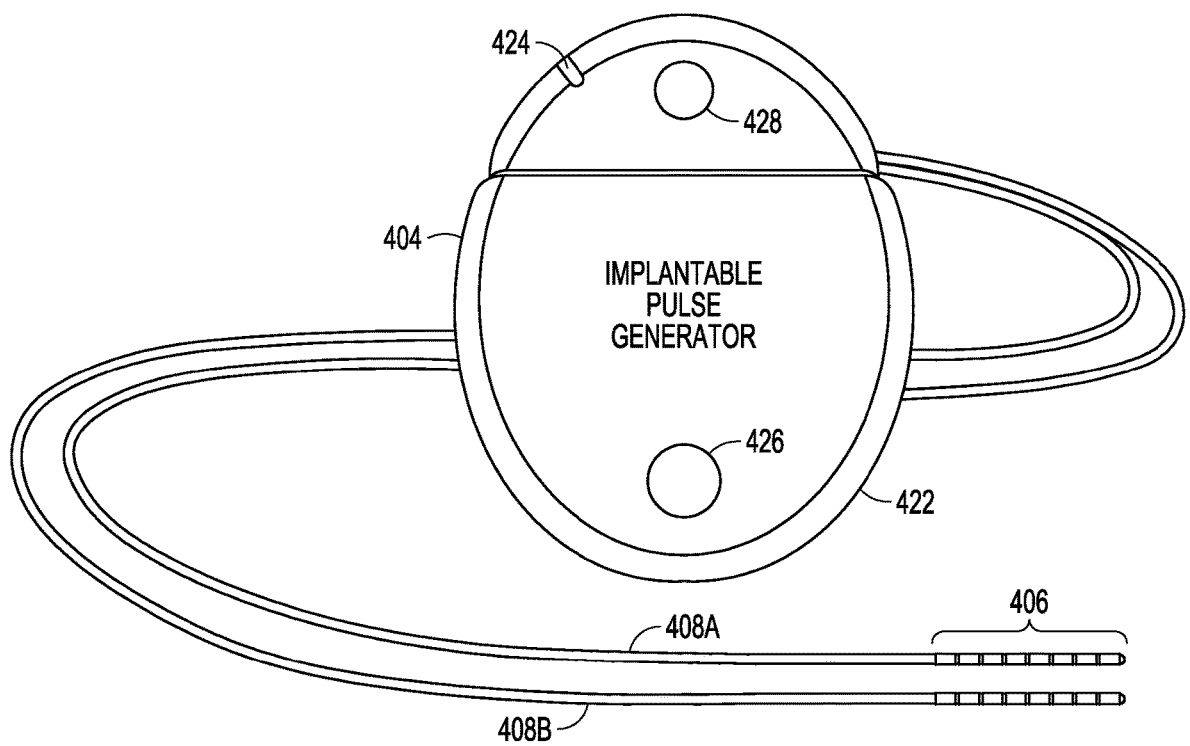
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to a nerve cell target included in the subject's spinal cord.

Figure 5:
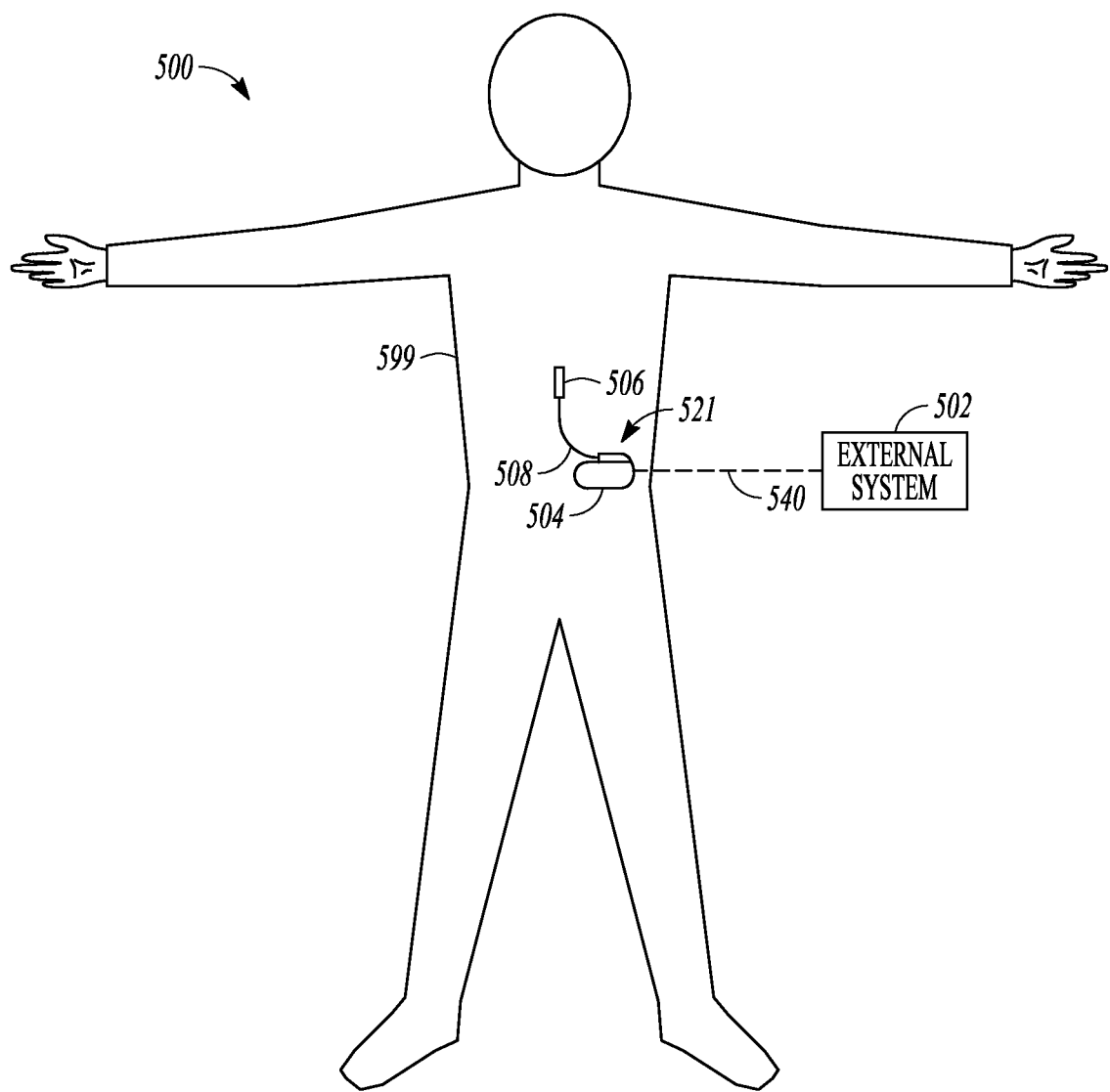
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
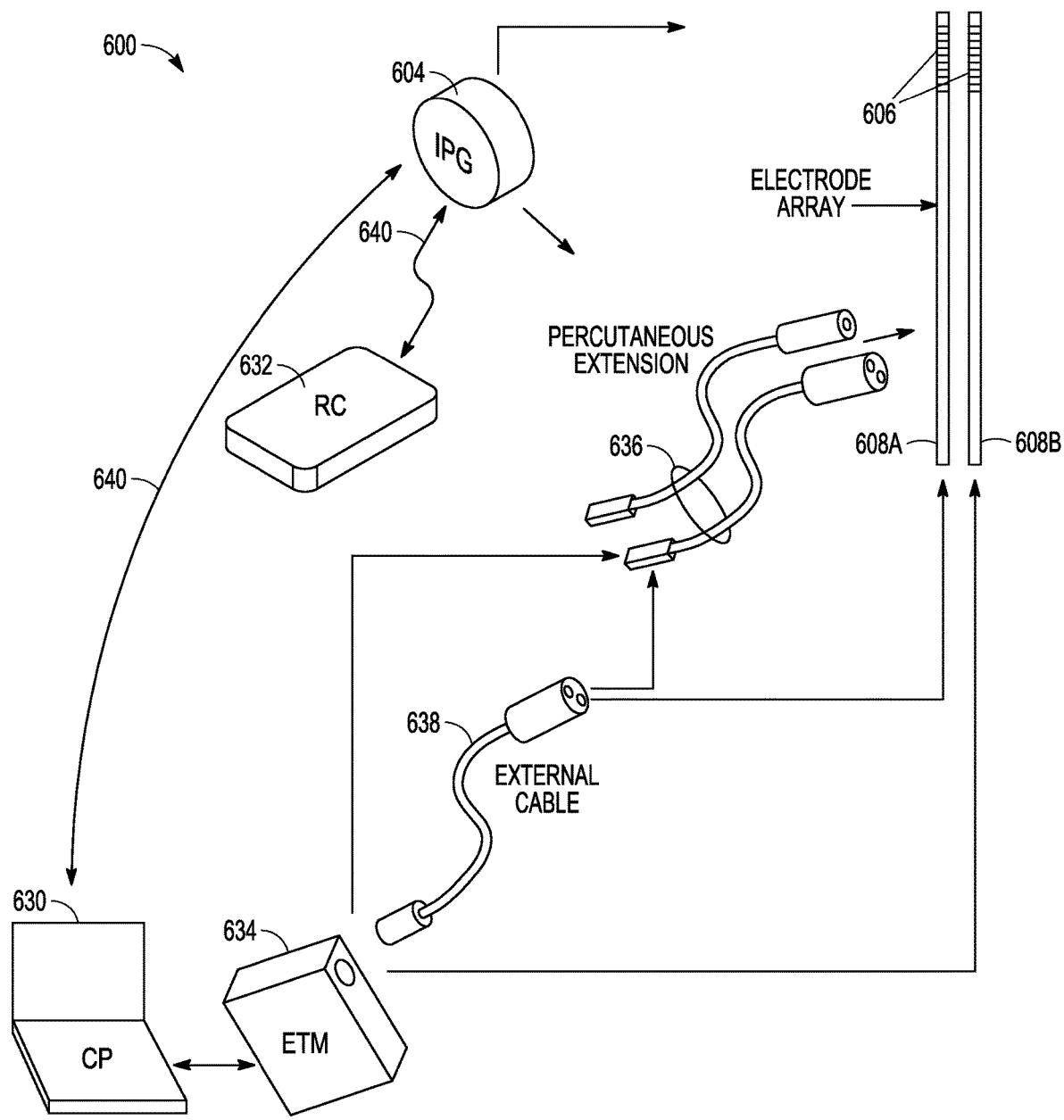
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, or ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
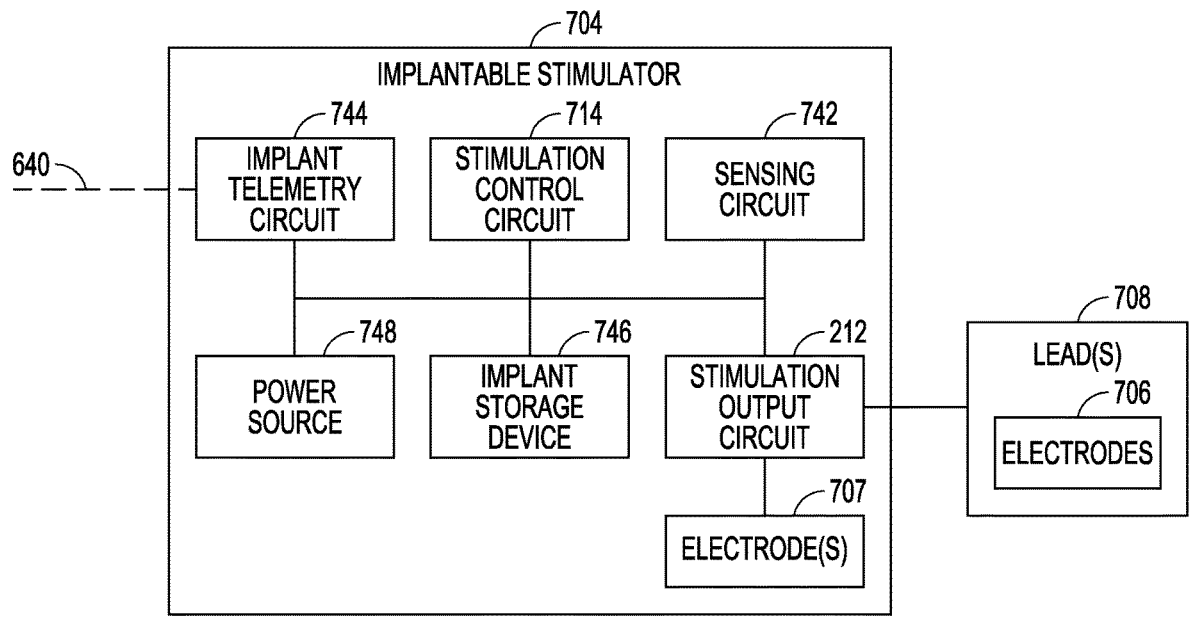
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters defining the pulse sequence. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
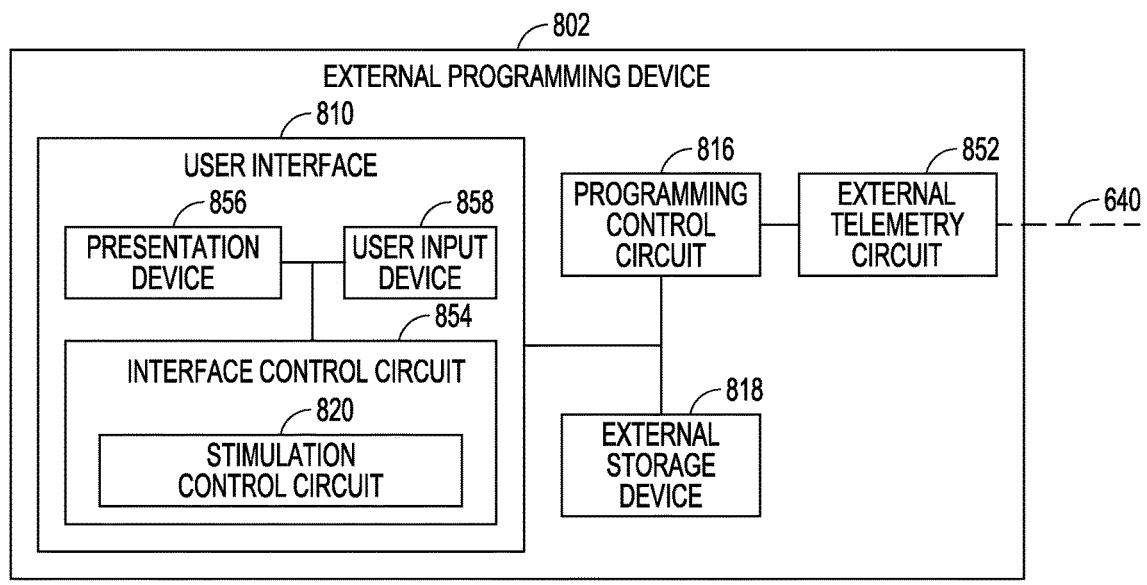
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a series of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters that defines one or more pulse sequences, which is to be transmitted to implantable stimulator 704, based on a specified neurostimulation program (e.g., the pulse sequence as represented by one or more stimulation waveforms and one or more stimulation fields, or at least certain aspects of the pulse sequence). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pulse sequence and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, mouse, and microphone. In one embodiment, user interface 810 includes a GUI. The GUI may also allow the user to perform any functions discussed in this document where graphical presentation and/or editing are suitable as may be appreciated by those skilled in the art. In one embodiment, user interface 810 provides for voice control of various functions by the user. User input device 858 can allow the user to enter various commands and/or other information by speech to perform any functions discussed in this document where voice control is suitable as may be appreciated by those skilled in the art.

Interface control circuit 854 controls the operation of user interface 810 including responding to various inputs received by user input device 858 and defining the one or more stimulation waveforms. Interface control circuit 854 includes a stimulation control circuit 820 that allows for programming of stimulation devices, such as implantable stimulator 704, to deliver neurostimulation according to one or more neurostimulation programs (or one or more pulse sequences) as discussed in this document. The one or more neurostimulation programs can each include one or more pulse sequences as discussed in this document.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

External programming device 802 can be used to generate a modulated pulse sequence and can program a stimulation device such as implantable stimulator 704 for delivering neurostimulation through electrodes 706 and/or 707 and control the delivery of the neurostimulation according to the modulated pulse sequence. Programming control circuit 816 can generate a plurality of stimulation parameters controlling delivery of the neurostimulation pulses according to a pulse sequence that includes a series of neurostimulation pulses. The pulse sequence can be defined by sequence parameters and one or more modulation functions each modulating a parameter of one or more adjustable parameters selected from the sequence parameters. The one or more modulation functions can each be defined as a function of time, a function of pulse number, or a function of order arrangement of groups of pulses. The sequence parameters can include waveform parameters and field parameters. The waveform parameters define a stimulation waveform of the series of neurostimulation pulses. The field parameters define a stimulation field associated with the stimulation waveform. The stimulation field specifies a distribution of a stimulation energy (e.g., in terms of current, voltage, or charge) over the electrodes for each pulse of the series of neurostimulation pulses. The one or more adjustable parameters can include one or more adjustable waveform parameters and one or more adjustable field parameters. The one or more adjustable waveform parameters allow for adjustment of the stimulation waveform. The one or more adjustable field parameters allow for adjustment of the stimulation field. The one or more modulation functions can include one or more waveform modulation functions and one or more field modulation functions. The one or more modulation functions can each modulate a parameter of the one or more adjustable waveform parameters and are each defined by waveform modulation parameters. The one or more field modulation functions can each modulate a parameter of the one or more adjustable field parameters and are each defined by field modulation parameters.

External storage device 818 can store the pulse sequence, including the sequence parameters and the one or more modulation functions. In various embodiments, a neurostimulation program can include one or more pulse sequences, and delivery of the neurostimulation pulses is controlled according to the neurostimulation program. External storage device 818 can store multiple pulse sequences and one or more neurostimulation programs each including one or more pulses sequences selected from the multiple pulse sequences. The stored multiple pulse sequences can each be a tonic pulse sequence (in which the one or more adjustable parameters each have a constant value) or a patterned pulse sequence (in which at least one of the one or more adjustable parameters has a value that varies over time). An example of the patterned pulse sequence includes the modulated pulse sequence as discussed in this document.

Presentation device 856 can present a modulation control panel allowing for selection of a parameter from the one or more adjustable parameters and determination of a modulation function of the one or more modulation functions. The determined modulation function is to be applied to the selected parameter. User input device 858 can receive user input for the determination of the modulation function using the presented modulation control panel. Stimulation control circuit 820 can create the pulse sequence according to the user input. In various embodiments, stimulation control circuit 820 can create a tonic pulse sequence by determining an initial value for each parameter of the one or more adjustable parameters, and can set the programmed pulse sequence to the tonic pulse sequence for adjusting or optimizing the one or more adjustable parameters. Stimulation control circuit 820 can also load a created (e.g., programmed or optimized) tonic sequence or import a shared or predefined tonic sequence. Stimulation control circuit 820 can then create or generate a modulated pulse sequence by selecting one or more parameters from the one or more adjustable parameters of the tonic pulse sequence, selecting a modulation function for each parameter of the selected one or more adjustable parameters, selecting or adjusting the relevant modulation parameters, and applying the determined modulation function to the each parameter to modulate the tonic pulse sequence, and can set the programmed pulse sequence to the modulated pulse sequence for controlling the delivery of the neurostimulation pulses to the patient.

The modulation control panel can be selected from a plurality of modulation control panels based on a type of the parameter selected from the one or more adjustable parameters. In various embodiments, presentation device 856 can present a waveform modulation control panel in response to a parameter of the one or more adjustable waveform parameters being selected and present a field modulation control panel in response to a parameter of the one or more adjustable field parameters being selected.

Figure 9:
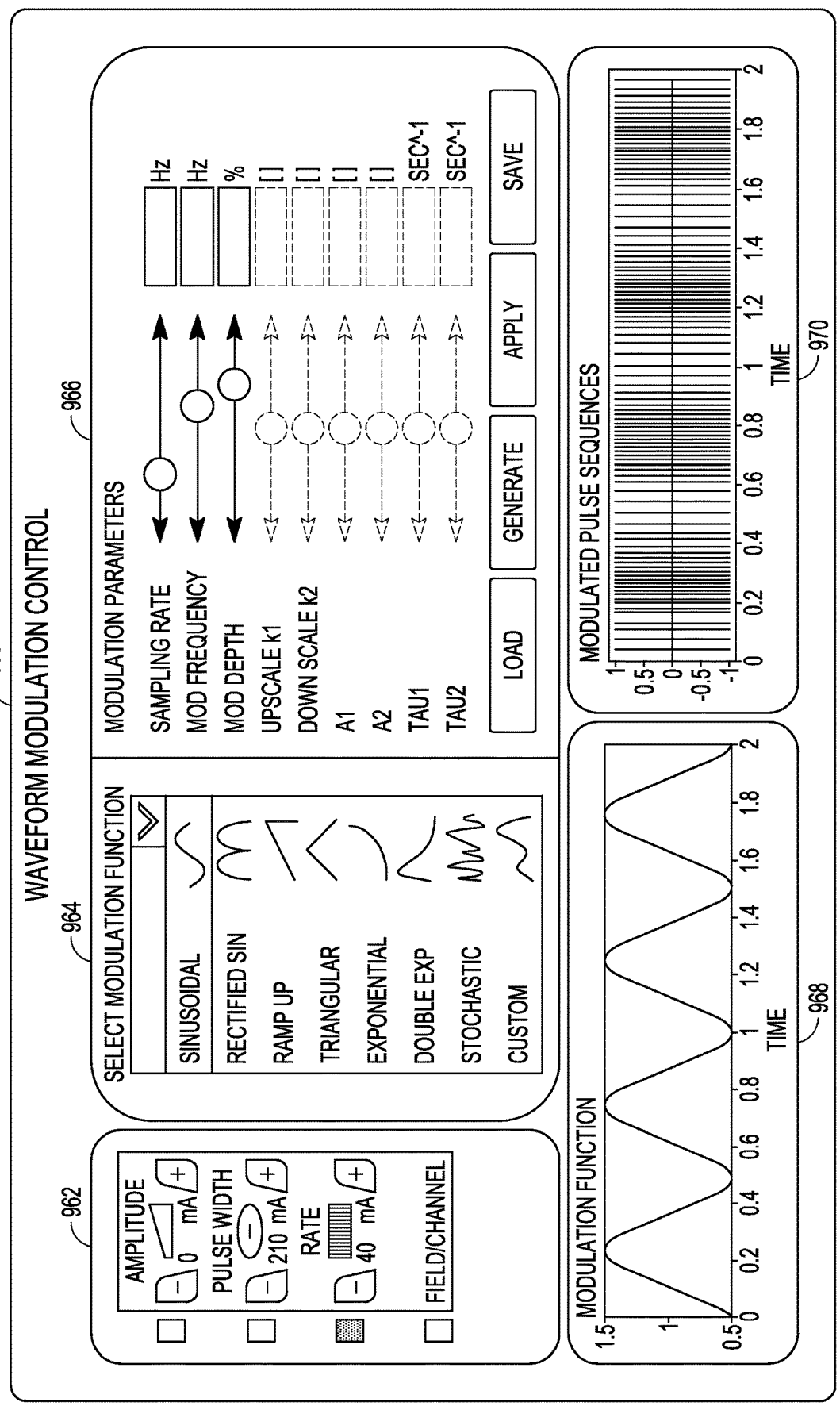
FIG. 9 illustrates an embodiment of a waveform modulation control panel (showing a sinusoidal modulation function being selected as an example) of a user interface of a programming device, such as the programming device of FIG. 3.

FIG. 9 illustrates an embodiment of a waveform modulation control panel 960 that can be presented using presentation device 856. Waveform modulation control panel 960 includes an adjustable parameters field 962, a waveform modulation function selection field 964, a waveform modulation parameters field 966, a waveform modulation function visualization field 968, and a modulated pulse sequence field 970. The contents and layout of waveform modulation control panel 960 are shown in FIG. 9 for illustrative purposes by way of example, but not by way of restriction. In various embodiments, waveform modulation control panel 960 can be configured to perform the function according to the present subject matter while satisfying various therapy control requirements (e.g., parameters to be adjustable and types of modulation functions needed) and design considerations (e.g., contents to be presented and their layout based on user preference and/or access control).

Adjustable parameters field 962 presents the one or more adjustable parameters and allow for selection and programming of the parameter from the presented one or more adjustable parameters using user input device 858. The one or more adjustable parameters include adjustable parameters defining a tonic pulse sequence. Neurostimulation pulses can be delivered to the patient according to the tonic pulse sequence, and the adjustable parameters can be adjusted or optimized based on the patient's response. In the illustrated embodiment, four adjustable parameters are selectable to be modulated, including three adjustable waveform parameters: pulse amplitude (AMPLITUDE), pulse width (PULSE WIDTH), and pulse rate (RATE) and an adjustable field parameter: stimulation field (FIELD/CHANNEL). The stimulation field can be identified by spatial configuration referring to an electrode setting including electrode selection and distribution of stimulation energy among the selected electrodes. The stimulation field can also be identified by a channel, referring to a channel of the stimulation output circuit through which selected pulses of the neurostimulation pulses are delivered.

When presented in waveform modulation control panel 960, adjustable parameters field 962 allows for selection of a parameter from the one or more adjustable (waveform and field) parameters. In response to the selected parameter being an adjustable waveform parameter, waveform modulation control panel 960 allows for determination of a waveform modulation function for modulating the selected parameter. In response to the selected parameter being an adjustable field parameter, waveform modulation control panel 960 is switched to the field modulation control panel (discussed below with reference to FIGS. 12-13).

Waveform modulation function selection field 964 presents available options of waveform modulation functions and allows for selection of an option from the available options of waveform modulation functions. For example, as illustrated in FIG. 9, the available options of waveform modulation functions can include sinusoidal, rectified sinusoidal, ramp-up, triangular, exponential, double-exponential, stochastic, and custom modulation functions. In various embodiments, the available options of waveform modulation functions can include any desirable standard, stochastic, and/or custom modulation functions. The list presented in waveform modulation function selection field 964 can also be adjusted based on user feedback, user preference, and/or continuous learning and knowledge build-up. In various embodiments, waveform modulation function selection field 964 allows for selection of an option from the available options of waveform modulation functions, modification of the modulation function of the selected option using user interface 810, and addition of a new option to the available options.

Waveform modulation parameters field 968 presents waveform modulation parameters associated with the selected waveform modulation function and allow for determination of the waveform modulation parameters. In various embodiments, waveform modulation parameters field 968 can present only the waveform modulation parameters associated with the selected waveform modulation function, or otherwise to present all but enable determination of only the waveform modulation parameters associated with the selected waveform modulation function. For example, the presented waveform modulation parameters include sampling rate, modulation frequency, modulation depth, up scale k1 and down scale k2 (associated with triangular function or ramp-up function), A1 and A2, and Tau1 and Tau 2 (associated with exponential and double-exponential functions). When the sinusoidal modulation function is selected (as shown in FIG. 9 as an example), the sampling rate, modulation frequency, and modulation depth are enabled to allow for adjustments using user input device 858, while the remaining waveform modulation parameters are disabled for adjustment. The waveform modulation parameters are applied to the selected modulation function to generate the modulation function for modulating the pulse sequence when, for example, the "Generate" button in waveform modulation parameters field 966 is hit.

Waveform modulation function visualization field 968 presents the selected waveform modulation function. The presented waveform modulation function is defined by the selected waveform modulation function as presented in waveform modulation function selection field 964 and the waveform modulation parameters associated with the selected modulation function as presented in waveform modulation parameters field 966. The presented waveform modulation function is updated in response to each change made in waveform modulation function selection field 964 or waveform modulation parameters field 966 (e.g., when the "Apply" button in waveform modulation parameters field 966 is hit).

Modulated pulse sequence field 970 presents the pulse sequence modulated by the selected waveform modulation function (as presented in waveform modulation function visualization field 968). The presented modulated pulse sequence is updated in response to each change made in waveform modulation function selection field 964 or waveform modulation parameters field 966 (e.g., when the "Apply" button in waveform modulation parameters field 966 is hit).

Figure 10:
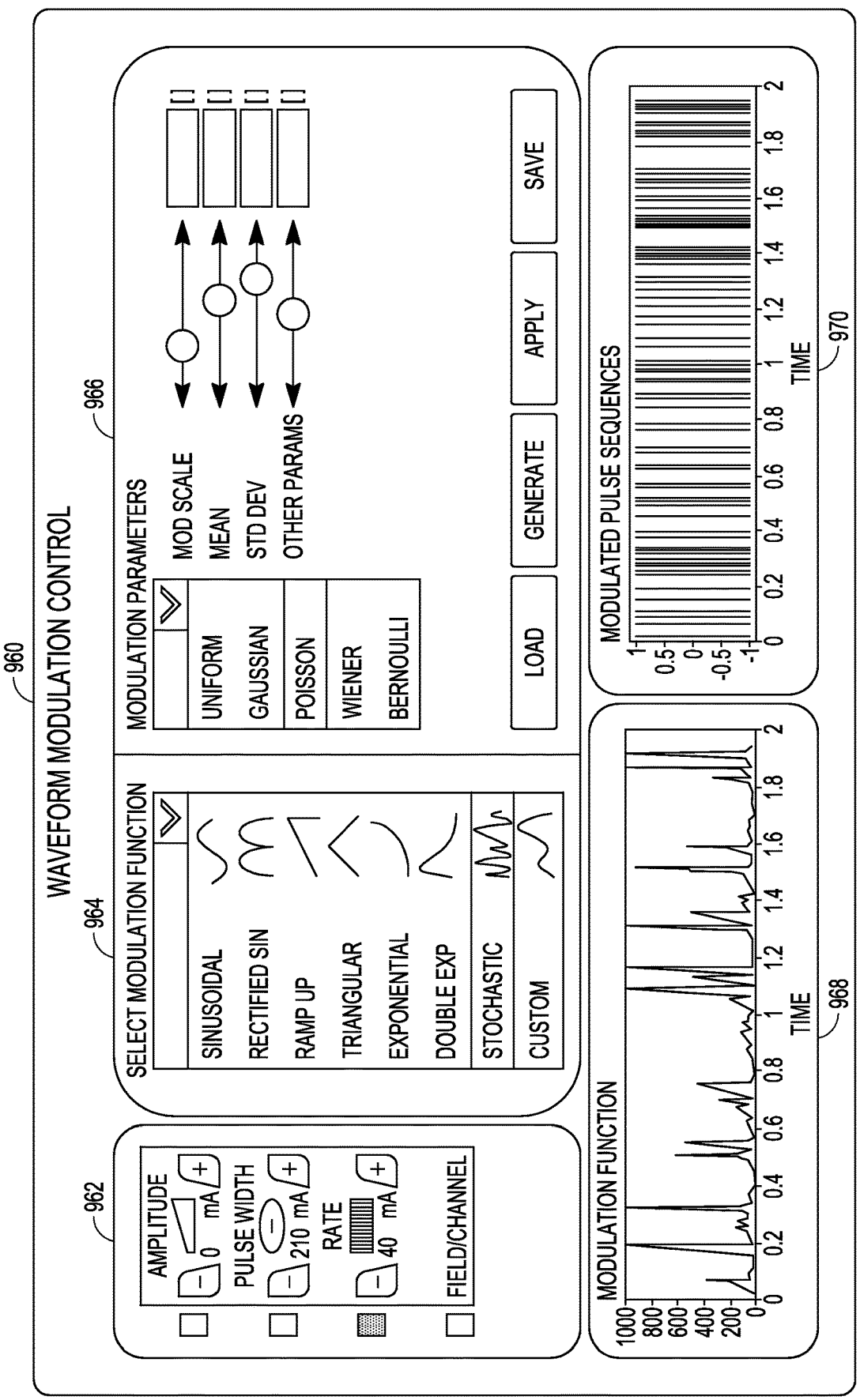
FIG. 10 illustrates an embodiment of the waveform modulation control panel of FIG. 9 showing a stochastic modulation function being selected.

FIG. 10 illustrates an embodiment of waveform modulation control panel 960 when the stochastic modulation function is selected. In response to the stochastic function being selected, waveform modulation parameters field 966 presents the modulation parameters associated with the stochastic function and allows for determination of the presented parameters. The modulation parameters can include types of distribution and parameters associated with each type of distribution. For example, as illustrated in FIG. 10, the types of distribution include uniform, Gaussian, Poisson, Wiener, and Bernoulli. When Poisson distribution is selected, the parameters presented to allow for adjustment include modulation scale, mean, standard deviation, and other parameters (e.g., other stochastic model related parameters such as range, upper boundary, lower boundary, percentile, and/or length/duration of the time series). The stochastic modulation function can also include a shuffled sequence of various pre-defined pulses.

Figure 11:
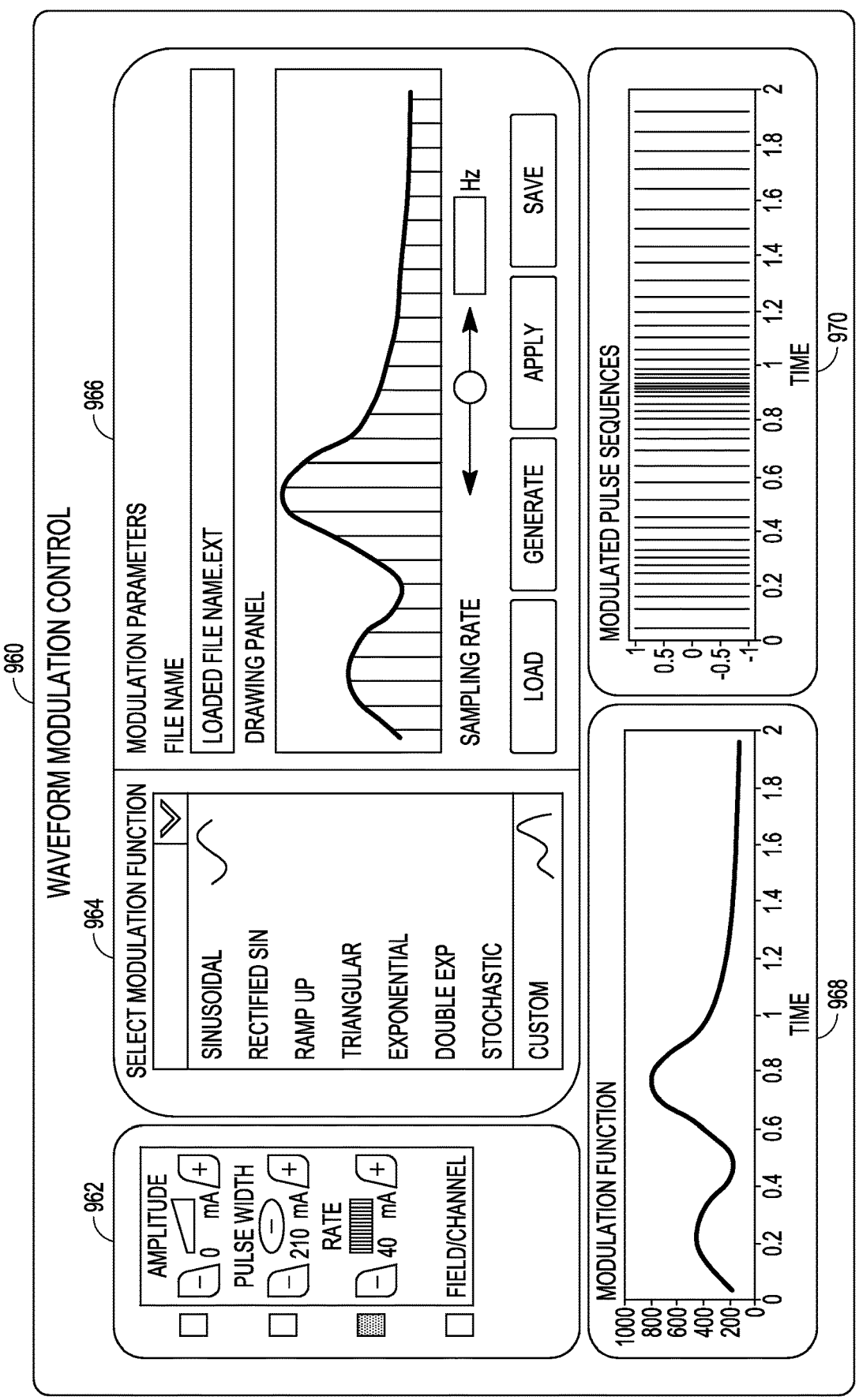
FIG. 11 illustrates an embodiment of the waveform modulation control panel of FIG. 9 showing a custom modulation function being selected.

FIG. 11 illustrates an embodiment of the waveform modulation control panel 960 when the custom modulation function is selected. In response to the custom modulation function being selected, waveform modulation parameters field 966 presents fields allowing for loading of a stored modulation function, creation of a custom modulation function, and storing of the created custom modulation function. The custom modulation function can be created by modifying a stored function, which can be a standard function (e.g., sinusoidal, rectified sinusoidal, ramp-up, triangular, exponential, or double-exponential function) or a previously created custom modulation function, or by accepting real time user input (e.g., drawing). In the illustrated embodiment, waveform modulation parameters field 966 includes a file name field, a drawing panel, and a sampling rate field. The file name field allows for specifying a stored modulation function for loading (e.g., by hitting "Load" button in waveform modulation parameters field 966) or assigning a file name identifying a created custom modulation function for storing (e.g., by hitting "Save" button in waveform modulation parameters field 966). The drawing panel allows for graphically creating and editing the custom modulation function. The custom modulation function can be created by drawing and/or editing a loaded stored function. The sampling rate field allows for adjustment of a sample rate at which the custom modulation field is sampled and applied to the selected adjustable parameter. The sampling rate determining a repeat rate for each pulse or block of the neurostimulation pulses because after each sampling, as the parameters defining the next pulse remain unchanged until the next sampling, i.e., the same pulse or block repeats between two consecutive samplings.

Figure 12:
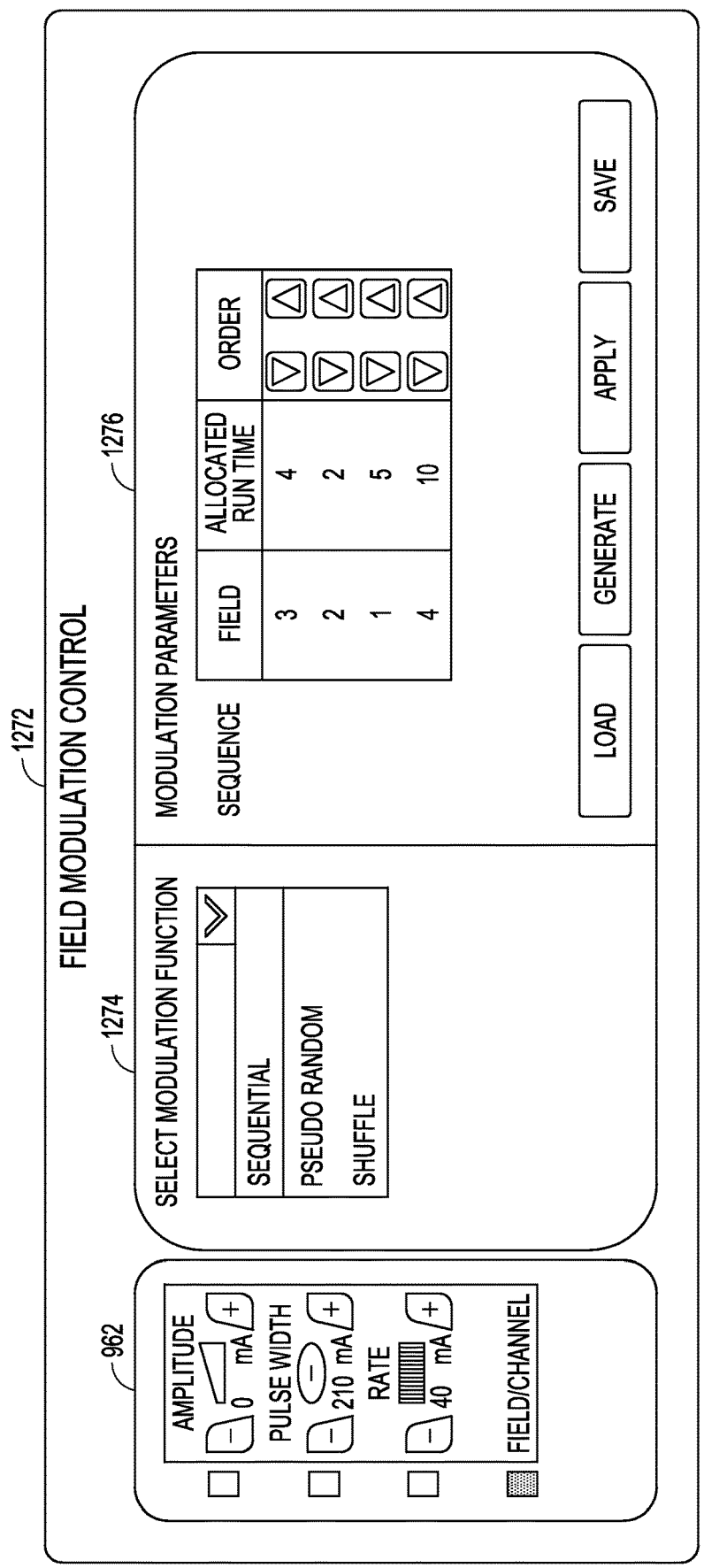
FIG. 12 illustrates an embodiment of a field modulation control panel (showing a sequential modulation function being selected as an example) of the user interface of FIG. 9.

FIG. 12 illustrates an embodiment of a field modulation control panel 1272 that can be presented using presentation device 856. Field modulation control panel 1272 includes adjustable parameters field 962, a field modulation function selection field 1274, and a field modulation parameters field 1276. The contents and layout of field modulation control panel 1272 are shown in FIG. 12 for illustrative purposes by way of example, but not by way of restriction. In various embodiments, field modulation control panel 1272 can be configured to perform the function according to the present subject matter while satisfying various therapy control requirements (e.g., parameters to be adjustable and types of modulation functions needed) and design considerations (e.g., contents to be presented and their layout based on user preference).

Adjustable parameter field 962 is included in both waveform modulation control panel 960 and field modulation control panel 1272. When presented in field modulation control panel 1272, adjustable parameters field 962 allows for selection of a parameter from the one or more adjustable (waveform and field) parameters. While the users may select one parameter at a time to apply the modulation function, multiple parameters can be modulated for a stimulation pulse sequence. Indicators (e.g., highlights) can be shown in the adjustable parameter field 962 to indicate which parameter(s) have already been selected with respective modulating function(s) applied. In response to the selected parameter being an adjustable field parameter, field modulation control panel 1272 allows for determination of a field modulation function for modulating the selected parameter. In response to the selected parameter being an adjustable waveform parameter, field modulation control panel 1272 is switched to the waveform modulation control panel 960.

Field modulation function field 1274 presents available field modulation functions and allows for selection of a field modulation function from the available field modulation functions. For example, as illustrated in FIG. 12, the available field modulation functions can include sequential (fields in predetermined order), pseudo random (fields in semi-randomized order), and shuffle (fields in randomized order) functions. In this document, field modulation functions can refer to various methods for modulating the stimulation field, including indexing functions.

Field modulation parameters field 1276 presents field modulation parameters associated with the selected field modulation function and allows for determination of the field modulation parameters. In various embodiments, field modulation parameters field 1276 can present only the field modulation parameters associated with the selected field modulation function or otherwise enable determination of only the field modulation parameters associated with the selected field modulation function. As illustrated in FIG. 12 for example, in response to the sequential modulation function being selected, field modulation parameters field 1276 presents a sequence of fields defined by the field modulation parameters including "field", "allocated run time", and "order". The field parameter can include a label identifying a field, (e.g., number 1, 2, . . . or alphabet A, B). The allocated run time parameter can include a number of repeats for each field on the list of fields, a duration for each field on the list of fields, a duty cycle, etc. (assuming the neurostimulation is cycling among multiple fields with difference times allocated for the fields. The order parameter allows the user to define the direction of field changes by adjusting the order of running for a list of fields (e.g., clockwise/counterclockwise, or up/down).

Figure 13:
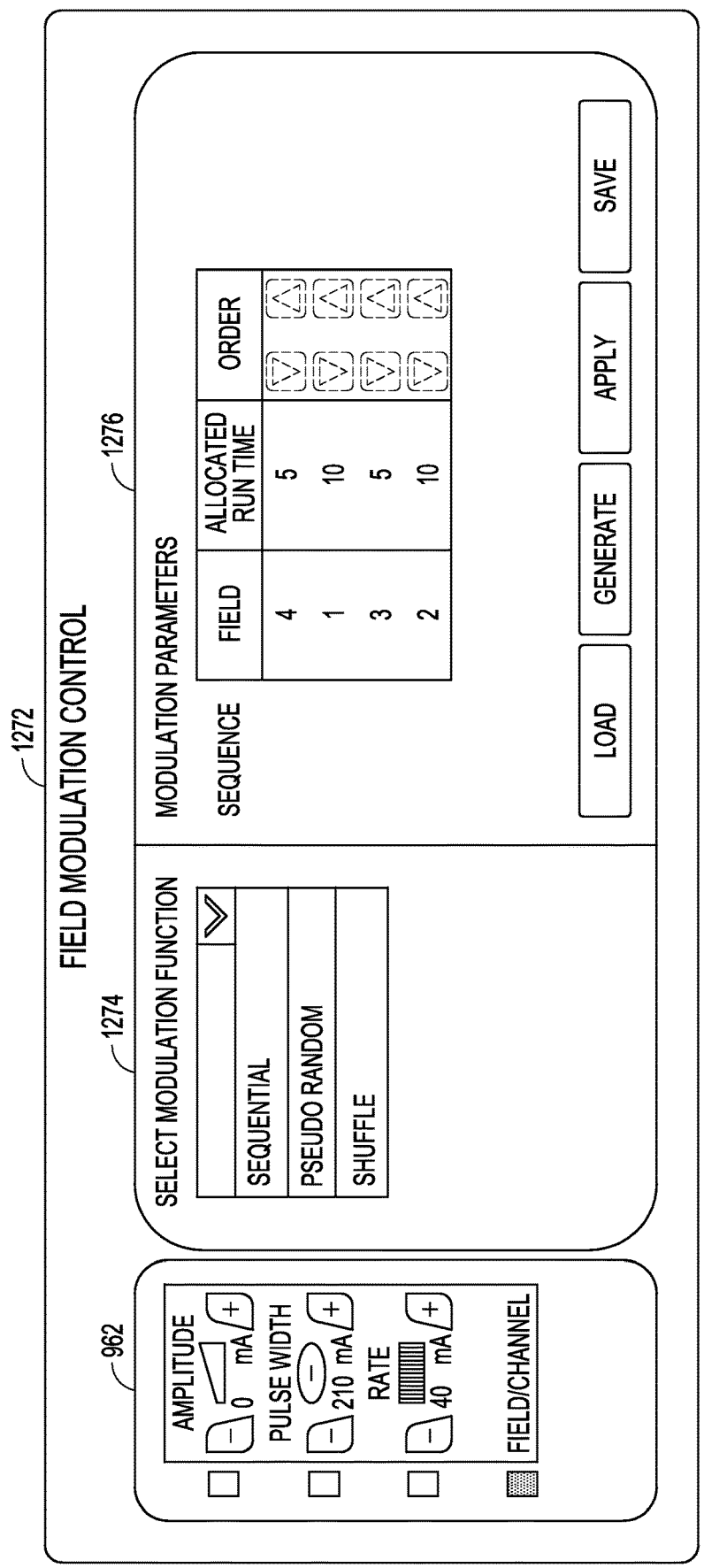
FIG. 13 illustrates an embodiment of the field modulation control panel of FIG. 12 showing a pseudo random modulation function being selected.

FIG. 13 illustrates an embodiment of field modulation control panel 1272 when the pseudo random modulation function is selected. Field modulation parameters field 1276 presents the same field modulation parameters for adjustments, but with the order parameter disabled because the order is pseudo random (e.g., one or more samples of permutations of a sequence that resembles a random order).

Figure 14:
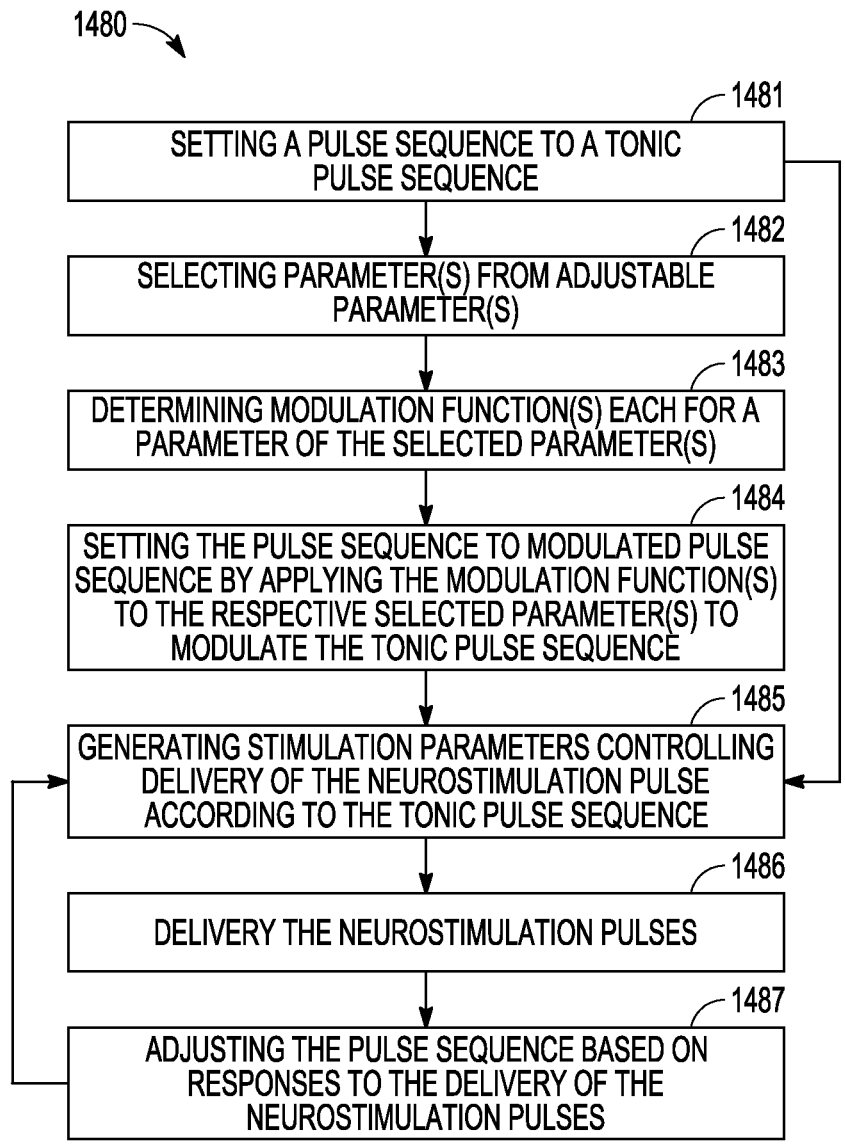
FIG. 14 illustrates an embodiment of a method for delivering neurostimulation according to a pulse sequence.

FIG. 14 illustrates an embodiment of a method 1480 for delivering neurostimulation according to a pulse sequence. Method 1480 can be performed using a system including a user interface and a storage device, such as user interface 810 and external storage device 818. In one embodiment, external storage device 818 can include a non-transitory computer-readable storage medium including instructions, which when executed by a processor on which interface control circuit 854 including stimulation control circuit 820 is implemented, cause the processor (or portion thereof, including stimulation control circuit 820) to perform method 1480. In various embodiments, method 1480 is performed for purposes of determining whether or how to deliver a neurostimulation therapy to a patient.

At 1481, the pulse sequence is set to a tonic pulse sequence (or another template pulse sequence). The pulse sequence includes a series of neurostimulation pulses and is defined by sequence parameters and one or more modulation functions each modulating a parameter of one or more adjustable parameters selected from the sequence parameters. The pulse sequence can be set to a tonic pulse sequence by determining an initial value for each parameter of the one or more adjustable parameters. The one or more adjustable parameters can include one or more adjustable waveform parameters and/or one or more adjustable field parameters. The one or more adjustable waveform parameters allow for adjustment of a stimulation waveform of the series of neurostimulation pulses. The one or more adjustable field parameters allow for adjustment of a stimulation field associated with the stimulation waveform. The stimulation field specifies a distribution of a stimulation energy (e.g., in terms of current, voltage, or charge) over the electrodes for each pulse of the series of neurostimulation pulses. The one or more modulation functions can include one or more waveform modulation functions and/or one or more field modulation functions. The one or more waveform modulation functions can each modulate a parameter of the one or more adjustable waveform parameters. The one or more field modulation functions can each modulate a parameter of the one or more adjustable field parameters. In various embodiments, the tonic pulse sequence can be optimized for each patient by adjusting the one or more adjustable parameters for a desirable response from the patient. The optimization can include a closed-loop control of the adjustment of the one or more adjustable parameters using responses sensed from the patient as feedback. At 1482, one or more parameters are selected from the one or more adjustable parameters. At 1483, one or more modulation functions are each determined for a parameter of the selected one or more parameters. At 1484, the pulse sequence is set to a modulated pulse sequence by applying the one or more modulation functions to the respective selected parameter(s) to modulate the tonic pulse sequence. In various embodiments, the modulated pulse sequence includes one or more sequence parameters each modulated by a modulation function (i.e., the one or more parameters selected from the one or more adjustable parameters). In various embodiments, step 1483 can include an iterative process of adjusting each modulation function to obtain a desirable response from the patient. The adjustment of the one or more modulation functions can include closed-loop control using responses sensed from the patient as feedback.

While the tonic sequence is discussed specifically as an example, the pulse sequence can be set to a template pulse sequence other than the tonic pulse sequence at 1481. In various embodiments, the template pulse sequence can be relevant or irrelevant to the modulated pulse sequence. The template pulse sequence can also be a waveform that can be used to generate a pulse sequence (e.g., a binary sequence representing timing of pulses or status of modulation).

In various embodiments, to perform steps 1482, 1483, and 1484, a user interface is used to present a modulation control panel allowing for selection of a parameter from the one or more adjustable parameters and determination of a modulation function of the one or more modulation functions. The determined modulation function is to be applied to the selected parameter. The user interface is also used to receive user input for the determination of the initial value for each parameter of the one or more adjustable parameters and the determination of the modulation function using the presented modulation control panel. Using the received user input, the user interface controls the presentation of the modulation control panel and generates the tonic pulse sequence and the modulated pulse sequence.

In various embodiments, the user interface is used to select the modulation control panel from a plurality of modulation control panels based on a type of the parameter selected from the one or more adjustable parameters. For example, a waveform modulation control panel is presented on the user interface in response to a waveform parameter of the one or more adjustable waveform parameters being selected, and a field modulation control panel is presented on the user interface in response to a field parameter of the one or more adjustable field parameters being selected. The waveform modulation control panel is used to receive the selection the parameter from the one or more adjustable waveform parameters, to allow for determination of a waveform modulation function for modulating the selected parameter in response to the selected parameter being the waveform parameter, and to switch to the field modulation control panel in response to the selected parameter being the field parameter. To determine a waveform modulation function, the waveform modulation control panel is used to present available waveform modulation functions, to receive selection of a waveform modulation function from the available waveform modulation functions, to present waveform modulation parameters associated with the selected waveform modulation function, and to allow for determination of the waveform modulation parameters. The field modulation control panel is used to receive the selection of the parameter from the one or more adjustable waveform parameters, to allow for determination of a field modulation function for modulating the selected parameter in response to the selected parameter being the field parameter, and to switch to the waveform modulation control panel in response to the selected parameter being the waveform parameter. To determine a field modulation function, the field modulation control panel is used to present available field modulation functions, to receive selection of a field modulation function from the available field modulation functions, to present field modulation parameters associated with the selected field modulation function, and to allow for determination of the field modulation parameters.

At 1485, stimulation parameters are generated for controlling delivery of neurostimulation pulses according to the pulse sequence. At 1486, the neurostimulation pulses are delivered. At 1487, the pulse sequence is adjusted based on responses to the delivery of the neurostimulation pulses. Steps 1485, 1486, and 1487 can be applied for delivery of the neurostimulation pulses according to the tonic pulse sequence or the modulated pulse sequence. The neurostimulation pulses can be delivered according to the tonic pulse sequence for adjusting the initial value for each parameter of the one or more adjustable parameters for the patient (e.g., to optimize the tonic pulse sequence for the patient using the responses and one or more optimization criteria specified for the tonic pulse sequence). The neurostimulation pulses can be delivered according to the modulated pulse sequence for adjusting the one or more modulation functions and/or the associated modulation parameters for the patient (e.g., to optimize the modulated pulse sequence for the patient using the responses and one or more optimization criteria specified for the modulated pulse sequence). This can include repeating some or all of the steps of method 1480. In various embodiments, the one or more optimization criteria can be specified as one or more thresholds or trend on measurable responses of the patient. Such measurable responses can include input from the patient and/or parameters measured from signals sensed from the patient in response to the delivery of the neurostimulation pulses, such as neural signals (e.g., evoked compound action potentials), other physiological signals, and physical activities.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation through electrodes to a patient, the system comprising:
    a programming control circuit configured to generate a plurality of stimulation parameters controlling delivery of the neurostimulation according to a pulse sequence, the pulse sequence including a series of neurostimulation pulses and defined by sequence parameters including one or more adjustable parameters; and
    a user interface coupled to the programming control circuit and configured to:
        set the pulse sequence to a tonic pulse sequence including an initial value for each adjustable parameter of the one or more adjustable parameters, including controlling the delivery of the neurostimulation according to the tonic pulse sequence and adjusting the one or more adjustable parameter to obtain a desirable response of the patient, the initial value determined for the each adjustable parameter for the delivery of the neurostimulation according to the tonic pulse sequence to produce the desirable response; and
        set the pulse sequence to a modulated pulse sequence by modulating the tonic pulse sequence including the initial value determined for the each adjustable parameter, including selecting one or more modulated parameters from the one or more adjustable parameters, determining a modulation function for each modulated parameter of the selected one or more modulated parameters, and applying the determined modulation function to the each modulated parameter to modulate the each modulated parameter in the tonic pulse sequence.

2. The system of claim 1, wherein the user interface comprises:
    a presentation device configured to present a modulation control panel allowing for selection of a parameter from the one or more adjustable parameters and determination of a modulation function of the one or more modulation functions, the determined modulation function to be applied to the selected parameter;
    a user input device configured to receive user input for the determination of the initial value for each adjustable parameter of the one or more adjustable parameters and the determination of the modulation function using the presented modulation control panel; and
    an interface control circuit configured to control the presentation of the modulation control panel and to create the tonic pulse sequence and the modulated pulse sequence using the received user input.

3. The system of claim 2, wherein the user interface is configured to present the modulation control panel of a plurality of modulation control panels based on a type of the parameter selected from the one or more adjustable parameters.

4. The system of claim 3, wherein the one or more adjustable parameters comprise at least one of:
    one or more adjustable waveform parameters allowing for adjustment of a stimulation waveform of the series of neurostimulation pulses, the one or more adjustable waveform parameters each to be modulated by a waveform modulation function of the one or more modulation functions; or
    one or more adjustable field parameters allowing for adjustment a stimulation field associated with the stimulation waveform, the stimulation field specifying a distribution of a stimulation energy over the electrodes for each pulse of the series of neurostimulation pulses, the one or more adjustable field parameters each to be modulated by a field modulation function of the one or more modulation functions;
    and wherein the user interface is configured to:
        present a waveform modulation control panel in response to a waveform parameter of the one or more adjustable waveform parameters being selected; and
        present a field modulation control panel in response to a field parameter of the one or more adjustable field parameters being selected.

5. The system of claim 4, wherein the waveform modulation control panel and the field modulation control panel each comprise an adjustable parameters field configured to display the one or more adjustable parameters and allow for selection of the parameter from the one or more adjustable parameters.

6. The system of claim 4, wherein the waveform modulation control panel is configured to:
    allow for the selection the parameter from the one or more adjustable waveform parameters and the one or more adjustable field parameters;
    allow for determination of a waveform modulation function for modulating the selected parameter in response to the selected parameter being the waveform parameter; and switch to the field modulation control panel in response to the selected parameter being the field parameter.

7. The system of claim 6, wherein the waveform modulation control panel comprises:
   a waveform modulation function selection field configured to present available waveform modulation functions and to allow for selection of a waveform modulation function from the available waveform modulation functions; and
   a waveform modulation parameters field configured to present waveform modulation parameters associated with the selected waveform modulation function and allow for determination of the waveform modulation parameters.

8. The system of claim 7, wherein:
   the waveform modulation control panel further comprises a waveform modulation function visualization field configured to present the selected waveform modulation function, the presented waveform modulation function defined by the selected waveform modulation function as presented in the waveform modulation function selection field and the waveform modulation parameters associated with the selected modulation function as presented in the waveform modulation parameters field; and
   the waveform modulation control panel further comprises a modulated pulse sequence field configured to present the pulse sequence modulated by the selected waveform modulation function.

9. The system of claim 4, wherein the field modulation control panel is configured to:
   allow for the selection of the parameter from the one or more adjustable waveform parameters and the one or more adjustable field parameters;
   allow for determination of a field modulation function for modulating the selected parameter in response to the selected parameter being the field parameter; and
   switch to the waveform modulation control panel in response to the selected parameter being the waveform parameter.

10. The system of claim 9, wherein the field modulation control panel comprises:
    a field modulation function field configured to present available field modulation functions and to allow for selection of a field modulation function from the available field modulation functions; and
    a field modulation parameters field configured to present field modulation parameters associated with the selected field modulation function and allow for determination of the field modulation parameters.

11. A method for delivering neurostimulation through electrodes to a patient, the method comprising:
    generating a plurality of stimulation parameters controlling delivery of the neurostimulation according to a pulse sequence, the pulse sequence including a series of neurostimulation pulses and defined by sequence parameters including one or more adjustable parameters;
    setting the pulse sequence to a tonic pulse sequence including an initial value for each adjustable parameter of the one or more adjustable parameters, including delivering the neurostimulation according to the tonic pulse sequence and adjusting the one or more adjustable parameters to obtain a desirable response of the patient, the initial value determined for the each adjustable parameter for the delivery of the neurostimulation according to the tonic pulse sequence to produce the desirable response;
    selecting one or more modulated parameters from the one or more adjustable parameters;
    determining one or more modulation functions each for a parameter of the selected one or more modulated parameters; and
    setting the pulse sequence to a modulated pulse sequence by modulating the tonic pulse sequence including the initial value determined for the each adjustable parameter, including applying the determined one or more modulation functions to the respective selected one or more modulated parameters to modulate the selected one or more modulated parameters in the tonic pulse sequence.

12. The method of claim 11, further comprising using a user interface to:
    present a modulation control panel allowing for selection of a parameter from the one or more adjustable parameters and determination of a modulation function of the one or more modulation functions, the determined modulation function to be applied to the selected parameter;
    receive user input for the determination of the initial value for each adjustable parameter of the one or more adjustable parameters and the determination of the modulation function using the presented modulation control panel; and
    control the presentation of the modulation control panel and create the tonic pulse sequence and the modulated pulse sequence using the received user input.

13. The method of claim 12, further comprising using the user interface to present the modulation control panel of a plurality of modulation control panels based on a type of the parameter selected from the one or more adjustable parameters.

14. The method of claim 13, wherein the one or more adjustable parameters comprise at least one of:
    one or more adjustable waveform parameters allowing for adjustment of a stimulation waveform of the series of neurostimulation pulses, the one or more adjustable waveform parameters each to be modulated by a waveform modulation function of the one or more modulation functions; or
    one or more adjustable field parameters allowing for adjustment a stimulation field associated with the stimulation waveform, the stimulation field specifying a distribution of a stimulation energy over the electrodes for each pulse of the series of neurostimulation pulses, the one or more adjustable field parameters each to be modulated by a field modulation function of the one or more modulation functions.

15. The method of claim 14, further comprising using the user interface to:
    present a waveform modulation control panel in response to a waveform parameter of the one or more adjustable waveform parameters being selected; and
    present a field modulation control panel in response to a field parameter of the one or more adjustable field parameters being selected.

16. The method of claim 15, further comprising using the user interface, while the waveform modulation control panel is presented, to:
    receive the selection the parameter from the one or more adjustable waveform parameters and the one or more adjustable field parameters;

allow for determination of a waveform modulation function for modulating the selected parameter in response to the selected parameter being the waveform parameter; and switch to the field modulation control panel in response to the selected parameter being the field parameter.

17. The method of claim 16, further comprising using the user interface, while the waveform modulation control panel is presented, to:

present available waveform modulation functions;

receive selection of a waveform modulation function from the available waveform modulation functions;

present waveform modulation parameters associated with the selected waveform modulation function; and allow for determination of the waveform modulation parameters.

18. The method of claim 15, further comprising using the user interface, while the field modulation control panel is presented, to:

receive the selection of the parameter from the one or more adjustable waveform parameters and the one or more adjustable field parameters;

allow for determination of a field modulation function for modulating the selected parameter in response to the selected parameter being the field parameter; and switch to the waveform modulation control panel in response to the selected parameter being the waveform parameter.

19. The method of claim 18, further comprising using the user interface, while the field modulation control panel is presented, to:

present available field modulation functions;

receive selection of a field modulation function from the available field modulation functions;

present field modulation parameters associated with the selected field modulation function; and allow for determination of the field modulation parameters.

20. A non-transitory computer-readable storage medium including instructions, which when executed by a system, cause the system to perform a method for delivering neurostimulation through electrodes to a patient, the method comprising:

generating a plurality of stimulation parameters controlling delivery of the neurostimulation according to a pulse sequence, the pulse sequence including a series of neurostimulation pulses and defined by sequence parameters including one or more adjustable parameters;

setting the pulse sequence to a tonic pulse sequence including an initial value for each adjustable parameter of the one or more adjustable parameters, including delivering the neurostimulation according to the tonic pulse sequence and adjusting the one or more adjustable parameters to obtain a desirable response of the patient, the initial value determined for the each adjustable parameter for the delivery of the neurostimulation according to the tonic pulse sequence to produce the desirable response;

selecting one or more modulated parameters from the one or more adjustable parameters of the tonic pulse sequence;

determining one or more modulation function each for a parameter of the selected one or more modulated parameters; and setting the pulse sequence to a modulated pulse sequence by modulating the tonic pulse sequence including the initial value determined for the each adjustable parameter, including applying the determined one or more modulation functions to the respective selected one or more modulated parameters to modulate the selected one or more modulated parameters in the tonic pulse sequence.

* * * * *